US006207877B1

(12) United States Patent
Dickneite et al.

(10) Patent No.: US 6,207,877 B1
(45) Date of Patent: Mar. 27, 2001

(54) TRANSGENIC COAGULATION FACTOR XIII DEFECTIVE ANIMAL AND ITS USE FOR TESTING WOUND HEALING AND BLEEDING

(75) Inventors: Gerhard Dickneite; Hubert Metzner, both of Marburg; Gerd Zettlmeissl; Ulrich Grundmann, both of Lahntal, all of (DE); Richard Lathe, Edinburgh (GB); Austin Smith, Edinburgh (GB); Meng Li, Edinburgh (GB)

(73) Assignee: Aventis Behring GmbH, Marburg (DE)

(*) Notice: Subject to any disclaimer, the term of this patent is extended or adjusted under 35 U.S.C. 154(b) by 0 days.

(21) Appl. No.: 09/404,208

(22) Filed: Sep. 23, 1999

(30) Foreign Application Priority Data

Sep. 23, 1998 (EP) .................................................. 98117978

(51) Int. Cl.[7] ...................... A01K 67/027; A01K 67/033; A01K 67/00; C12N 15/00; G01N 33/00
(52) U.S. Cl. .................................... 800/18; 800/3; 800/8; 800/13; 800/21
(58) Field of Search .................................. 800/13, 3, 21, 800/8; 514/44; 435/455

(56) References Cited

FOREIGN PATENT DOCUMENTS

| 0 236 978 A2 | 9/1987 | (EP) . |
| 69896/87 | 9/1987 | (AU) . |
| WO 91/16931 | 11/1991 | (WO) . |
| WO 94/04669 | 3/1994 | (WO) . |
| WO 97/46669 | 12/1997 | (WO) . |

OTHER PUBLICATIONS

Monsonego et al. FASEB 12:1163–1171, Sep. 1998.*
Ebert et al. Molecular Endocrinology 2(3):277–283, Feb. 1988.*
Hammer et al. Journal of ANimal Science 63:269–278, Jul. 1988.*
Schwaab et al. Thrombosis Research 61:225–234, Jan. 1991.*
Mullins et al. Journal of Clinical Investigations 98(11S):S37–S40, Sep. 1998.*
Moreadith et al. Journal of Molecular Medicine 75:208–216, Sep. 1998.*
Mustoe, T.A. et al., "Accelerated Healing of Incisional Wounds in Rats Induced by Transforming Growth Factor–β", Science, vol. 237, pp. 1333–1336, (1987).
Duckert, F., "Documentation of the Plasma factor XIII Deficiency in Man", Ann. NY Acad of Sci, vol. 202, pp. 190–199, (1972).
McDonagh, J., "Structure and Function of Factor XIII", *Hemostasis and Thrombosis: Basic Principles and Clinical Practice*, Third Edition, Lippincott Company, Philadelphia, pp. 301–313, (1994).
Karges, H. E., "Blood Coagulation Facto III: Determination by Clot Stability Assays", Bergmeyer: Methods of Enzymatic Analyses, Third Edition, vol. V, Verlag Chemie, Weinheim, pp. 400–410, (1984).
Anwar, Rashida et al., "Molecular Basis of Inherited Factor XIII Deficiency: Identification of Multiple Mutations Provides Insights Into Protein Function", British Journal of Haematology, vol. 91, pp. 728–735 (1995).
Ichinose, Akitada et al., "Arg260–Cys Mutation in Severe Factor XIII Deficiency: Conformational Change of the A Subunit is Predicted by Molecular Modelling and Mechanics", British Journal of Haematology, vol. 101, pp. 264–271 (1998).
Mikkola, Hanna et al., "Deficiency in the A–Subunit of Coagulation Factor XIII: Two Novel Point Mutations Demonstrate Different Effects on Transcript Levels", The American Society of Hematology, pp. 517–525 (1994).
Izumi, Tomonori et al., "Novel Deletion and Insertion Mutations Cause Splicing Defects, Leading to Severe Reduction in mRNA Levels of the A Subunit in Severe Factor XIII Deficiency," Throm Haemost, 79, pp. 479–485 (1998).
Rosier, Florence, "Les Souris<<Knockout>> Ont La Pêche", Genetique, pp. 48–50 (1996

* cited by examiner

Primary Examiner—Karen Hauda
Assistant Examiner—Joseph T. Woitach
(74) Attorney, Agent, or Firm—Finnegan, Henderson, Farabow, Garrett and Dunner, L.L.P.

(57) ABSTRACT

The invention provides a transgenic mouse which is heterozygous or homozygous for an at least partially defective coagulation factor XIII gene.

7 Claims, 4 Drawing Sheets

Sequence Alignment of Exon 7 of Mouse and Rat Factor XIII

```
                          ▽
         ——————————————————————————————————————
                 10           20           30
Mu       G T G A A T G C C A A G G A T G A T G A A G G T G T T C T T   30
Rat      G T G A A T G C C A A G G A T G A C G A A G G T G T T C T T   30

——————————————————————————————————————
                 40           50           60
Mu       G T T G G A T C A T G G G A C A A T G T C T A T G C C T A C   60
Rat      G T T G G A T C A T G G G A C A A T G T C T A T G C C T A C   60

▽
         ——————————————————————————————————————
                 70           80           90
Mu       G G C T C C C T T C C A T C A G C C T G G A C A G G A A G T   90
Rat      G G A T C C C T T C C A T C A G C C T G G A C A G G A A G T   90

▽
         ——————————————————————————————————————
                100          110          120
Mu       G T T G A C A T T C T A C T A G A A T A C A G A A G C T C G   120
Rat      G T T G A C A T T C T A C T A G A A T A C A G A A G C T C A   120

▽
         ——————————————————————————————————————
                130          140          150
Mu       G A A A C A C C A G T C C G A T A T G G C C A G T G T T G G   150
Rat      G A A A C A C C A G T C C G A T A T G G C C A G T G C T G G   150

——————————————————————————————————————
                160          170
Mu       G T T T T T G C T G G T G T C T T T A A C A C A               174
Rat      G T T T T T G C T G G T G T C T T T A A C A C A               174
```

TRANSGENIC COAGULATION FACTOR XIII DEFECTIVE ANIMAL AND ITS USE FOR TESTING WOUND HEALING AND BLEEDING

This invention relates to a transgenic non-human mammalian animal which is heterozygous or homozygous for an at least partially defective coagulation factor XIII gene.

Factor XIII is an enzyme of the coagulation cascade which cross-links fibrin and thus promotes the stability of the hemostatic plug.

The coagulation is a cascade system of proteolytic enzymes with subsequent activation by limited proteolysis. After wounding the intrinsic and the extrinsic pathways of coagulation are activated. The intrinsic activation includes coagulation factors XII, XI and IX which are proteolytic enzymes (proteases) and an enzyme cofactor (factor VIII). The extrinsic system includes tissue factor and factor VII. Both activation pathways result in the common pathway containing the protease factor Xa and its cofactor (factor Va) which convert the inactive prothrombin (factor II) to the enymatically active thrombin (IIa, n.b.: activated factors are marked with an "a" after the roman number, the roman number alone marks the inactive enzyme). Thrombin is considered to be the central protease of the coagulation system. It cleaves fibrinogen (factor I) resulting in fibrin which is the substrate for the wound closure. Together with blood platelets fibrin forms the hemostatic plug. Thrombin moreover activates the clotting factor XIII by limited proteolysis. In contrast to the other proteases of the coagulation cascade, factor XIII is a transglutaminase. Factor XIII cross-links the fibrin molecule via lysine and glutamine residues, rendering soluble fibrin into insoluble fibrin.

FXIII as found in plasma is composed to two nonidentical subunits, the a-chain and b-chain, with molecular weights of approximately 83.000 and 76.500 Da respectively (McDonagh J., in: Hemostasis and Thrombosis, Colman R W, Hirsh J., March V. J. and Salzmann E. W. (eds), Lippincoft, Philadelphia, 1994).

The tetrameric complex in plasma has the composition $a_2b_2$ with a Mr of 320 000 Da. The concentration of the tetramer in plasma is about 0.07 $\mu$mol/l. During the activation step, thrombin cleaves an Arg-Gly bond at the positions 37 and 38 of the a-chain releasing a Mr 4500 activation peptide from the amino terminus. The b-chain dimer dissociates from the complex to release the active a-chain dimer ($a_2^*$, FXIIIa). FXIIIa is a glutamine-lysine transferase. The reaction, catalyzed is the formation of an isopeptide bond between the $\gamma$-carbonyl group of glutamine and the $\epsilon$-amino group of lysine between fibrin molecules, stabilizes the fibrin network. Four to six lysyl-glutamyl crosslinks are formed per mole of fibrin.

The lack of factor XIII in patients might lead to hemorrhagic diathesis and impairment of wound healing (Duckert F., Ann NY Acad Sci, vol. 202, 190–199, 1972). Patients with a congenital FXIII deficiency suffer from soft tissue and joint hemorrhage after trauma. The most serious form of bleeding is in the central nervous system, FXIII deficient patients have a high incidence of intracranial hemorrhage. Women with a FXIII deficiency often undergo abortion during pregnancy. FXIII stimulates the proliferation of fibroblasts, which is essential for wound healing. Thus, patients with FXIII deficiency were reported to have abnormal wound healing.

In this invention the generation of a transgenic coagulation factor XIII defective mouse with disturbance of the wound healing process and bleeding disorders is described. Furthermore, its use is described to develop wound healing accelerating drugs or drugs normalizing coagulation.

A transgenic animal which carries an at least partially defective coagulation factor XIII gene may be prepared by known gene manipulations, in which the factor XIII gene will be inactivated by an insertion, deletion, substitution or inversion or other suitable genetic manipulations. In the performance of the present invention a transgenic animal with a defective coagulation factor XIII gene has been prepared by a targeted disruption of the gene for the factor XIIIa subunit with deletion of the active site encoding the exon 7 sequence.

Thus, according to another aspect of the present invention there is provided a method of producing a transgenic non-human mammalian animal with an at least partially defective coagulation factor XIII gene comprising:

1. preparing a DNA construct encoding an at least partially defective coagulation factor XIII gene;
2. introducing such DNA construct into suitable carrier cells;
3. identifying cells in which the DNA construct has integrated by homologous recombination;
4. inserting those targeted cells into an embryo;
5. placing the embryo into a mother animal, and allowing the embryo to develop to full term;
6. deriving offsprings heterozygous for the disrupted factor XIIIa gene, and
7. interbreeding heterozygous offsprings to obtain animals homozygous for the defective factor XIIIa gene.

BRIEF DESCRIPTION OF THE DRAWINGS

FIG. 2: Sequence alignment of the mouse and rat Factor XIII sequences over the 174 base pairs of exon 7.

A transgenic mouse has been prepared as follows:

Preparation of a transgenic mouse

Homologous recombination in embryonic stem (ES) cells was employed to generate mice deficient for factor XIII.

Figure 1:
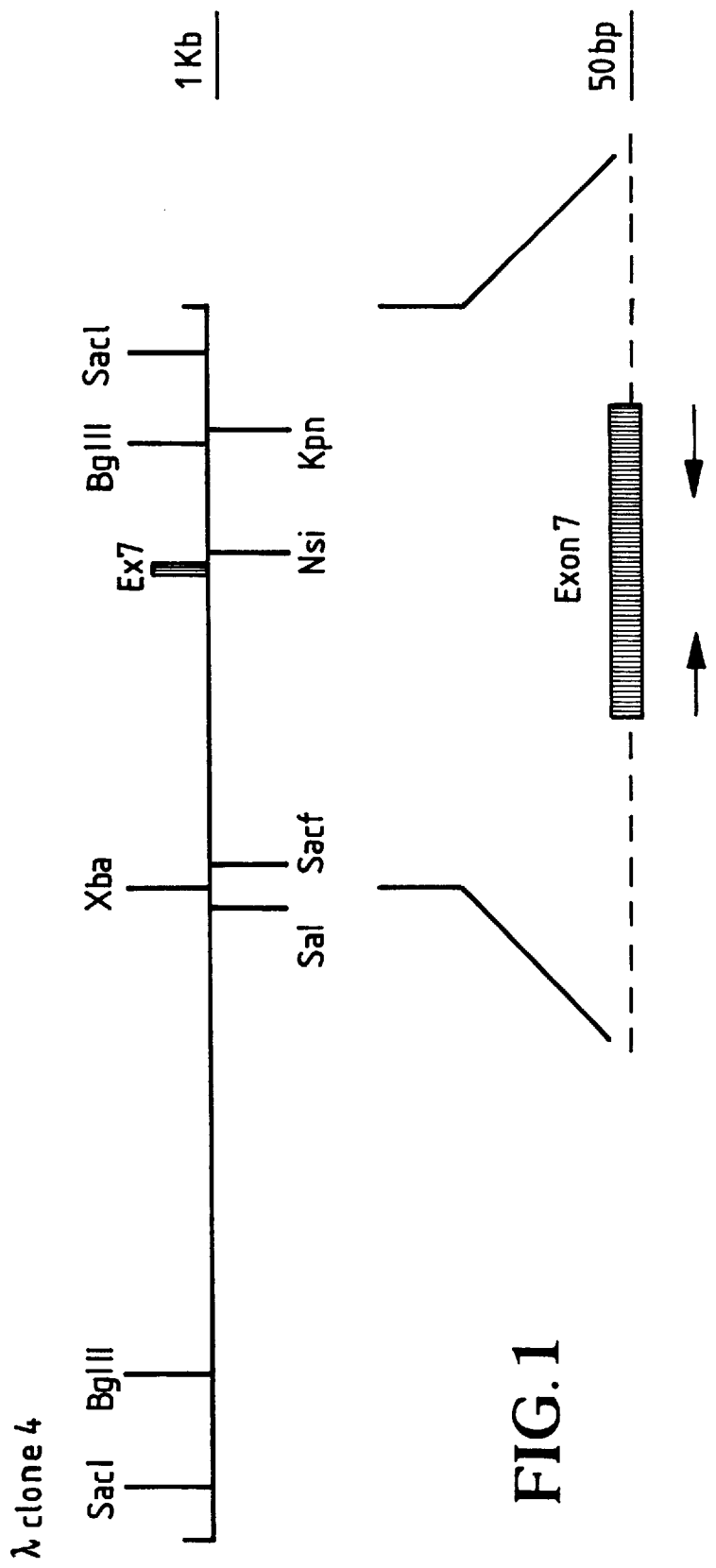
FIG. 1: Schematic drawing of the lambda clone 4 containing exon 7 of Factor XIII. The Xba/BamHI fragment containing exon 7 was subcloned into pBluescript and confirmed by double strand sequencing with the appropriate primers (arrows).

Mouse genomic sequences for the factor XIIIa subunit were isolated from a strain 129 genomic library using rat cDNA sequence as probe. A probe specific for the active site encoding exon (exon 7) was generated by PCR amplification of a 110 bp cognate fragment of the rat cDNA. This probe was used to isolate a 14 kb lambda clone (FIG. 1). The presence of mouse factor XIII exon 7 sequence Seq. ID. NO. 1 was confirmed by DNA sequencing which revealed 170/174 nucleotide identities with the rat exon 7 sequence Seq. ID. No. 2 (FIG. 2 and Sequence Listing). The encoded amino acid sequence is completely identical to the rat protein sequence.

Figure 3:
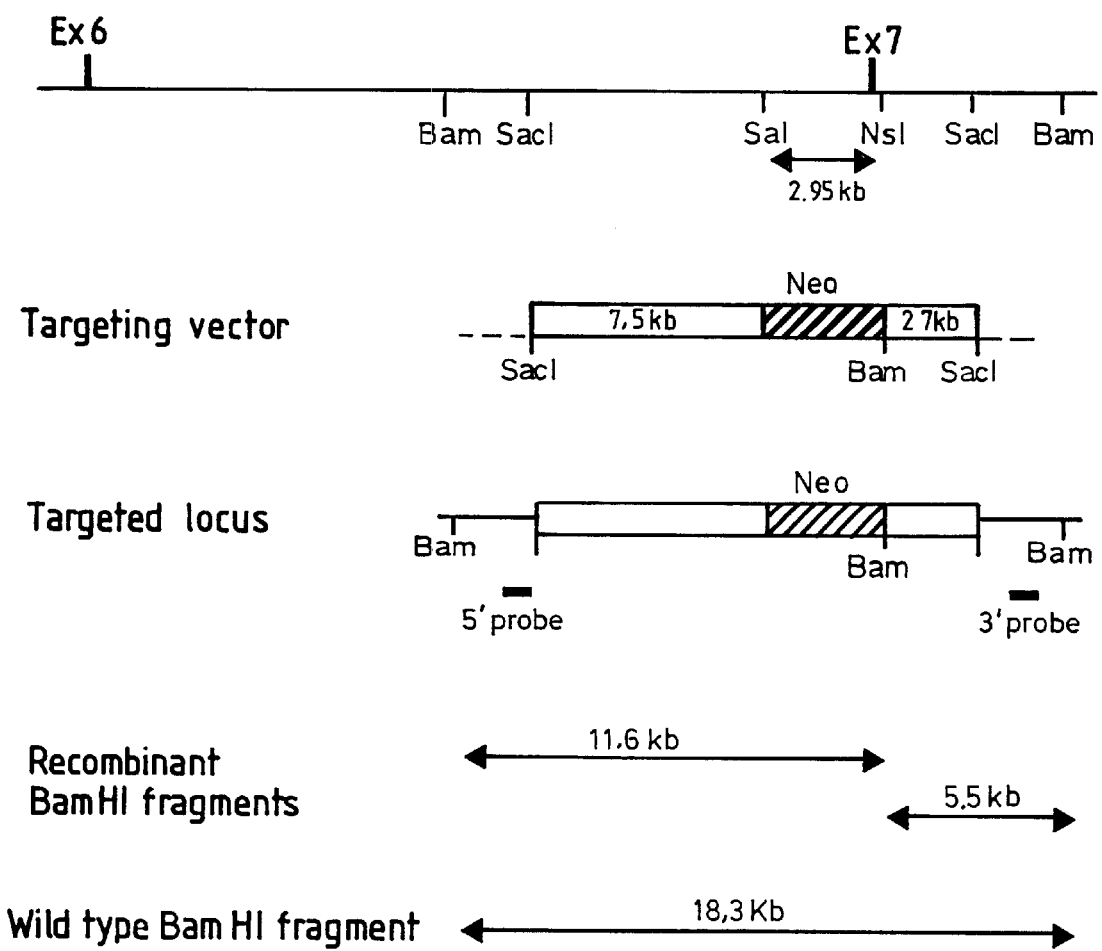
FIG. 3: Schematic drawing of the deletion vector for Factor XIII exon 7. Listed are the targeting vector, 5' and 3' probes, and predicted BamHI restriction fragments used to determine clones which underwent homologous recombination.
Figure 4:
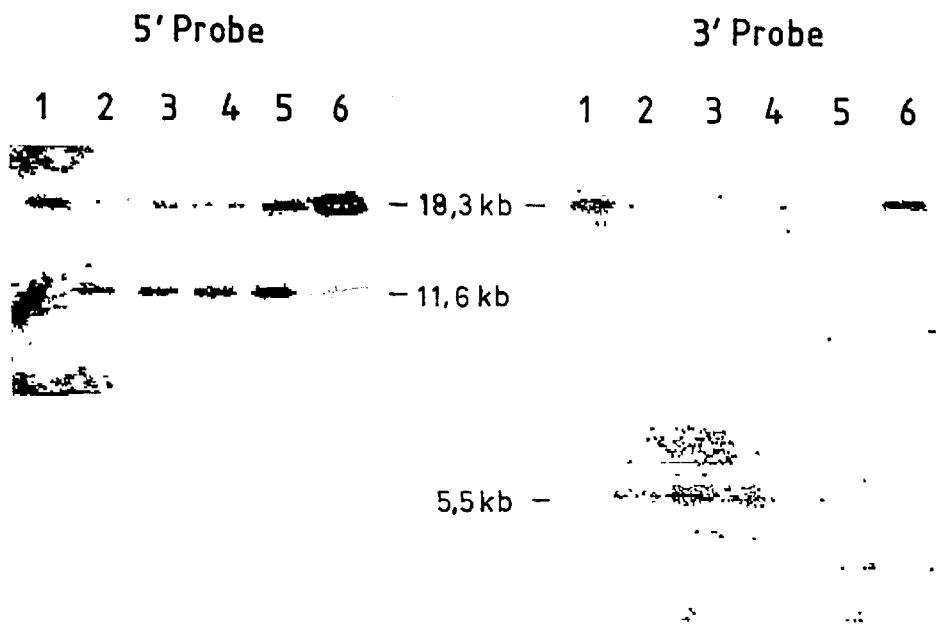
FIG. 4: Southern blot analysis of several ES cell clones. 5' and 3' probes are used to demonstrate a targeted deletion in several clones. Parental ES cell and a random insertion are included as controls.

A replacement type targeting vector was constructed using standard recombinant DNA methods. An approximately 2.95 kb region of genomic DNA encompassing exon 7 is deleted in the targeting construct and replaced by a b-actin promoter driven neomycin phosphotransferase selectable marker cassette (FIG. 3). The targeting construct was digested with Sac 1 to excise the plasmid sequences, then introduced into E14TG2a ES cells by electroporation. Stable transfectants were isolated by selection in G418. Homologous recombinants were identified by Southern hybridisation of genomic DNA with probes external to both 5' and 3' homology regions (FIG. 4). From two independent electroporations 4 out of 278 clones analysed gave the predicted hybridisation pattern for the homologous replacement event. Two of these clones (FXIII-110 and FXIII-129) were microinjected into C57BL/6 blastocyts to produce chimaeras. Chimaeras were initially test-crossed with outbred Swiss albino mice. Germline transmission was obtained from both clones.

Transmitting chimaeras were crossed with CBA/Ca mice to derive 12901a×CBA offspring carrying the mutated gene for the Factor XIIIa subunit. Following a backcross generation to CBA/Ca, heterozygous mice were intercrossed. Homozygous animals were identified by Southern hybridisation. The absence of exon 7 sequence in the homozygotes was confirmed using an exon 7 specific probe.

Said mouse has been characterized by its transglutaminase activity.

Characterization of the factor XIII defective mouse by its transglutaminase activity Venous blood was withdrawn and citrate plasma was obtained by centrifugation for further testing of transglutaminase activity. The assay used was the commercially available Berichrom F XIII kit, manufactured by Behring Diagnostics. As reference material human standard plasma has been used. Table 1 shows the results of the plasma transglutaminase determinations of normal mice with the same genetic background but without the defect in the FXIII gene, of hetereozygous FXIII defective mice and of homozgygous FXIII defective mice. The transglutaminase levels of the normal mice determined by Berichrom FXIII was 134%, for the heterozygous deficient animals the level determined was roughly half of that (70%). The transglutaminase levels of the homozygous FXIII defective mice was <6% . This could be confirmed with another FXIII assay, a clot stability assay where the FXIII activity is determined more specifically by its cross-linking activity towards fibrin which is rendered insoluble in urea or TCA solutions. With this assay no FXIII activity was detectable with a limit of detection of 2%.

TABLE 1

Transglutaminase levels in plasma of FXIII defective mice and normal control mice

| | Transglutaminase activity as % of standard human plasma |
| --- | --- |
| normal mice | 134% ± 10.4% |
| heterozygous FXIII defective mice | 70% ± 13.1% |
| homozygous FXIII defective mice | <6%* |

*£ 2% with a clot stability assay (H. E. Karges: Blood Coagulation Factor XIII: determination by clot stability assays. In: Bergmeyer: Methods of Enzymatic Analyses, Third Ed. Vol. V; Verlag Chemie, Weinheim, 1984; pp 400–410)

Use of the FXIII defective mouse—as a model for impaired wound healing and bleeding FXIII defective mice were anaesthetized with hexobarbital and the dorsal area was shaved. A full thickness midline incision of the skin was made with a surgical blade along the spine. The wound was then closed with clips and the mice were allowed to wake up from anaesthesia.

Two days later the clamps were removed. At 7, 9, and 16 days after wounding the tensile strength of the healed wound was investigated for each animal.

Mice were sacrified and the dorsal skin was removed. The skin was then cut into pieces of exactly one centimeter width and 3 centimeter length with centrally located incisions. The skin piece was then introduced into a tensiometer (Hounsfield Test Equipment, Salford, Redhill, England) and the tensile strength of the incision wound was measured according to the method described by Mustoe et. a. (Science, vol. 237, 1333–1336, 1987). A force was applied across the incision by tearing with a constant speed. The force was recorded graphically and the breaking strenght was defined as the point of maximum stress before wound separation.

The breaking strength was given in Newton (N). As a control we used a mouse strain with the same genetic background without the inserted defect gene (=normal mice), which underwent the same experimental procedure.

Table 2 shows the results of the wound healing study. Compared to the control there was lower breaking strength in the FXIII defective mice when compared to normal mice. This clearly indicates an impaired wound healing.

TABLE 2

Breaking strength of skin pieces from FXIII defective mice and normal control mice (Strain CBA)

| | normal mice (N) | FXIII defective mice (N) |
| --- | --- | --- |
| day 7 | 1.03 ± 0.09 | 0.69 ± 0.11 |
| day 9 | 2.3 ± 0.22 | 1.46 ± 0.14 |
| day 16 | 5.2 ± 0.03 | 3.3 ± 0 |

The test of the bleeding time serves as a measure of the hemostatic function. For the bleeding time the tail was resected at about 2 mm apart from the tip (tail tip bleeding). The time until cessation of bleeding was monitored by blotting the blood from the wound with a filter paper. Bleeding time was given in seconds for termination of bleeding. Table 3 denotes the results of the bleeding time. FXIII defective mice had a significantly prolonged bleeding time in comparison to normal mice.

TABLE 3

Bleeding time in FXIII defective mice and normal mice

| | Bleeding time (sec.) |
| --- | --- |
| normal mice | 170 ± 3 |
| FXIII defective mice | 274 ± 50 |

What is claimed is:

1. A transgenic mouse whose genome comprises a defective coagulation factor XIII gene, wherein said defective coagulation factor XIII gene comprises the inactivation of the endogenous coagulation factor XIII gene with a DNA construct, wherein said defective coagulation factor XIII gene results in a reduced level of transglutaminase activity which causes impaired wound healing and bleeding disorders in said mouse.

2. A transgenic mouse according to claim 1, wherein said DNA construct comprises a defective coagulation factor XIII gene comprising an insertion, deletion, substitution, or inversion.

3. A transgenic mouse according to claim 1, wherein said DNA construct comprises a defective coagulation factor XIII gene comprising a deletion of the active site of exon 7.

4. A transgenic mouse whose genome comprises a defective coagulation factor XIII gene comprising a deletion of the active site of exon 7, wherein said defective coagulation factor XIII gene comprises the inactivation of the endogenous coagulation factor XIII gene with a DNA construct, wherein said defective coagulation factor XIII gene results in a reduced level of transglutaminase activity.

5. A method of producing a transgenic mouse in accordance with claim 1 comprising:
   (a) preparing a DNA construct for inactivation of the factor XIII gene;
   (b) introducing said DNA into mouse embryonic cells;
   (c) identifying the cells into which the construct has integrated by homologous recombination;
   (d) inserting those targeted cells into a mouse embryo;
   (e) placing the embryo into a pseudopregnant mouse and allowing the embryo to develop to full term;
   (f) deriving offspring heterozygous for the defective coagulation factor XIII gene, and
   (g) interbreeding heterozygous offspring to obtain a mouse homozygous for the defective factor XIII gene, wherein said defective factor XIII gene results in a lack of transglutaminase activity which causes impaired wound healing and bleeding disorders.

6. A method of using the transgenic mouse of claim 1 for the testing of the pharmacological properties of a compound in relation to its coagulation factor XIII activity associated with a deficiency in coagulation factor XIII, the method comprising:
   (a) contacting the transgenic mouse with said compound, and
   (b) monitoring its effect on coagulation factor XIII activity by determining the effect on the wound healing process and bleeding disorders on said mouse.

7. A method of using the transgenic mouse of claim 1 for the investigation of an orally or parenterally administered pharmaceutical on wound healing, bleeding or other disorders associated with a deficiency in coagulation factor XIII comprising the steps of:
   (a) administering to said transgenic mouse said pharmaceutical, and
   (b) determining the effect on wound healing or bleeding disorders of said pharmaceutical on said mouse.

* * * * *

SEQUENCE LISTING

<160> NUMBER OF SEQ ID NOS: 2

<210> SEQ ID NO 1
<211> LENGTH: 174
<212> TYPE: DNA
<213> ORGANISM: Mus musculus

<400> SEQUENCE: 1

```
gtgaatgcca aggatgatga aggtgttctt gttggatcat gggacaatgt ctatgcctac  60
ggctcccttc catcagcctg gacaggaagt gttgacattc tactagaata cagaagctcg 120
gaaacaccag tccgatatgg ccagtgttgg gttttgctg  gtgtctttaa caca        174
```

<210> SEQ ID NO 2
<211> LENGTH: 174
<212> TYPE: DNA
<213> ORGANISM: Rattus rattus

<400> SEQUENCE: 2

```
gtgaatgcca aggatgacga aggtgttctt gttggatcat gggacaatgt ctatgcctac  60
ggatcccttc catcagcctg gacaggaagt gttgacattc tactagaata cagaagctca 120
gaaacaccag tccgatatgg ccagtgctgg gttttgctg  gtgtctttaa caca        174
```